United States Patent [19]

Boehringer et al.

[11] Patent Number: 5,409,491
[45] Date of Patent: Apr. 25, 1995

[54] APPARATUS AND METHOD FOR SHAPING BONE

[75] Inventors: John R. Boehringer, Wynnewood; John Karpowicz, Glenmoore; Sean Kerr, King of Prussia; Dana C. Mears, Pittsburgh, all of Pa.

[73] Assignee: Boehringer Laboratories, Inc., Norristown, Pa.

[21] Appl. No.: 5,887

[22] Filed: Jan. 15, 1993

[51] Int. Cl.⁶ ............................................. A61B 17/14
[52] U.S. Cl. ..................................... 606/82; 606/79; 606/178
[58] Field of Search .................. 606/82, 79, 176, 177, 606/178, 179; 30/123.3, 516, 515, 388, 392, 393, 394; 83/169, 171

[56] References Cited

U.S. PATENT DOCUMENTS

| | | |
|---|---|---|
| 1,628,315 | 5/1927 | Hamilton . |
| 2,463,014 | 9/1944 | Bem ..................................... 30/516 |
| 2,557,364 | 6/1951 | Treace . |
| 2,854,981 | 10/1958 | Morrison . |
| 3,554,197 | 1/1971 | Dobble . |
| 4,008,720 | 2/1977 | Brinckmann et al. . |
| 4,148,236 | 4/1979 | Holoyen et al. ......................... 83/74 |
| 4,567,798 | 2/1986 | Brdicko ..................................... 83/71 |
| 4,664,165 | 5/1987 | Pollack et al. ..................... 144/117 R |
| 4,729,763 | 3/1988 | Henrie ..................................... 604/22 |
| 4,961,359 | 10/1990 | Dunham ................................ 83/169 |
| 5,084,971 | 2/1992 | Remington ........................... 30/123 |
| 5,087,261 | 2/1992 | Ryd et al. ............................... 606/82 |
| 5,122,142 | 6/1992 | Pascaloff ................................ 606/82 |
| 5,133,728 | 7/1992 | Petersen ................................ 606/176 |
| 5,201,749 | 4/1993 | Sachse et al. ......................... 606/177 |

FOREIGN PATENT DOCUMENTS

| | | |
|---|---|---|
| 768337 | 5/1954 | Germany . |
| 2427716 | 11/1975 | Germany .............................. 606/82 |
| 162803 | 5/1954 | Sweden . |

*Primary Examiner*—Stephen C. Pellegrino
*Assistant Examiner*—Guy V. Tucker
*Attorney, Agent, or Firm*—Paul & Paul

[57] ABSTRACT

Apparatus and method is provided for shaping bone, in which, individually or together, a gaseous fluid such as air is delivered along the shaping member to impinge upon aerosols created by the shaping of the bone and to deliver the aerosols back toward the bone away from an operator, and a cooling liquid is delivered along the shaping member, in order to cool the shaping member where it contacts the bone. Preferably, the gaseous fluid is air and it is delivered through a manifold carried by the shaping member, forming an air curtain. Preferably, the cooling liquid is at least partially water, with or without a curative substance carried therein, with the liquid preferably being delivered through the shaping member and opening in a direction toward the shaped bone. Where the shaping member is a saw, the liquid may be delivered through the interior of the saw, for discharge through at least one narrow side thereof. Alternatively, the cooling liquid may be delivered externally of the saw. Various refinements are also provided in the form of valves, deflectors and means for exhausting heat and/or cut-away material from the site of operation.

23 Claims, 2 Drawing Sheets

APPARATUS AND METHOD FOR SHAPING BONE

BACKGROUND OF THE INVENTION

This invention relates to the shaping of bone. One technique of bone shaping is by resort to a saw, often an oscillating saw, but it will be understood that, in the broadest context, this invention relates not only to the sawing of bone, but also to various types of other abrading such as burr removal, reaming, grinding, cutting, milling, drilling, scraping, and even to electro-surgery and laser cutting devices.

Typically, such shaping equipment is used in orthopedics, and most often involves the use of saws to machine off portions of bone to fit prosthetics such as are used, for example only, in artificial knees and hips. Such shaping apparatus, often saws, are also used to cut pieces of bone out of hip sites, in order to form or shape a splice or fixation piece for operations on the spine, for example. Such pieces of bone must be extensively sawed and milled to shape.

In the course of such operations, the death or necrosis of bone tissue can be experienced any time the temperature resulting from shaping exceeds 130° F. for any significant period of time. When such necrosis occurs, the tissue does not grow into the cut site, fracture site, or surface of the cementless prosthesis or other prosthesis and knit. In the absence of knitting, the prosthesis may not be anchored by bone growth, possibly resulting in the necessity to have a replacement operation some period of years thereafter, often called a "revision procedure." In some instances, half of all knee or hip operations may be revision procedures, often because in the initial operation, where temperature is a contributing factor, excessive temperatures were reached at the site of the shaped surface or bone kerf (or cut).

It has in the past been recognized that it would be desirable to cool the shaping devices during their operation, in order to keep heat build-up at a minimum. To such an end, it is known to apply fluid such as water to the tool by external means, such as by a syringe, in order to attempt to cool the tool at the shaping site.

U.S. Pat. No. 2,557,364 represents a prior art surgical saw blade.

U.S. Pat. Nos. 4,008,720 and 5,087,261 represent bone saws of the type in which an oscillating blade driver drives a bone saw in an oscillating motion, and in which means are provided for delivering a cooling liquid to the bone site. Such prior art devices either do not deliver cooling liquid directly to the cutting site, or provide limitations in the type of shaping member due to the manner of liquid delivery.

It has also been found in connection with the shaping of bone, and particularly where a liquid is provided during such bone shaping for purposes of cooling the saw or other shaping member, that sprays or aerosols are generated. Such generation of sprays (or aerosols) at the site of the shaped bone (or kerf) create dangerous conditions, because of the dissemination of infections that might be present in the bone tissue, to the medical personnel attending the operation. For example, such infection might include hepatitis, AIDS, or the like. Prior art bone shaping apparatus and methods do not appear to have effectively addressed this serious concern.

To the extent that the prior art appears to have addressed the prevention of the dissemination of aerosols having the effluent of bone shaping, such as blood and tissue therein, such have generally proven to be inadequate. For example, mechanical barriers, such as transparent screens, may be provided, but visibility may be partially blocked as aerosols land on the screens, and such visibility becomes detrimental to the operation. Consequently, in many cases, mechanical barriers are not utilized, and the medical personnel may often be observed with red, moist aerosol-caused accumulations of blood and tissue on their gowns, masks and caps, at the end of an operation.

THE PRESENT INVENTION

The present invention is directed to providing a cooling liquid along the shaping member, at one or more of its narrow sides, through one or more conduits in the narrow sides, opening toward the abraded bone surface. Additionally, various valving, manifold, and scavenging features are provided.

The present invention also addresses the problem of potential dissemination of infection through aerosols that are caused at the site of the bone shaping, due to liquid cooling or otherwise, in providing apparatus and method for containment of the aerosols generally at the site of the operation, rather than dissemination into the surrounding air and possible contact with medical personnel. In doing so, the present invention provides for the impingement of a gaseous fluid, preferably air delivered to the site of bone shaping, with the aerosols that are emanating from the shaped bone surface, and driving the aerosols back away from the shaping apparatus (and personnel handling or attending the same) toward the bone. In accordance with this invention, an air (or other gaseous fluid) manifold is provided in association with the shaping apparatus. Such generally occurs by making an air curtain, preferably flowing around the entire tool in a direction toward the bone kerf or site of the shaping.

With the control of the aerosols resulting from bone shaping that is allowed by the present invention, the present invention allows the use of higher speed, rotating and oscillating tools with fluid introduced near their cutting edges, and even allows the use of increased cooling liquid because of such higher speeds of shaping, without fear that such high levels of liquid cooling will create too high a level of aerosols for the medical personnel to work in conditions of relative safety.

SUMMARY OF THE INVENTION

The present invention is directed to providing a bone shaping apparatus and method, in which gaseous fluid is supplied in conjunction with the shaping, for impingement of the gaseous fluid with aerosols emanating from the abraded bone kerf, and/or the cooling of the shaped bone surface along at least one conduit associated with a shaping member, which conduit opens in the direction of the shaping end of the member at a narrow side thereof, toward the portion of the bone being shaped.

Accordingly, it is a primary object of this invention to provide a novel bone shaping apparatus and method having the ability to contain aerosols generated at the site of bone shaping, by means of impingement of such aerosols by a gaseous fluid provided at the site of shaping.

It is another object of this invention to provide an enhanced liquid cooling technique and apparatus for a bone shaping operation.

It is a further object of this invention to provide each of the above objects, together.

It is yet another object of this invention to accomplish the above objects, wherein gaseous fluid for aerosol impingement and cooling liquid are provided via suitable manifold means associated with the shaping apparatus.

Other objects and advantages of the present invention will be readily apparent upon a reading of the following brief descriptions of the drawing figures, the detailed descriptions of the preferred embodiments, and the appended claims.

BRIEF DESCRIPTION OF THE DRAWING FIGURES

DETAILED DESCRIPTION OF THE PREFERRED EMBODIMENTS

Figure 1:
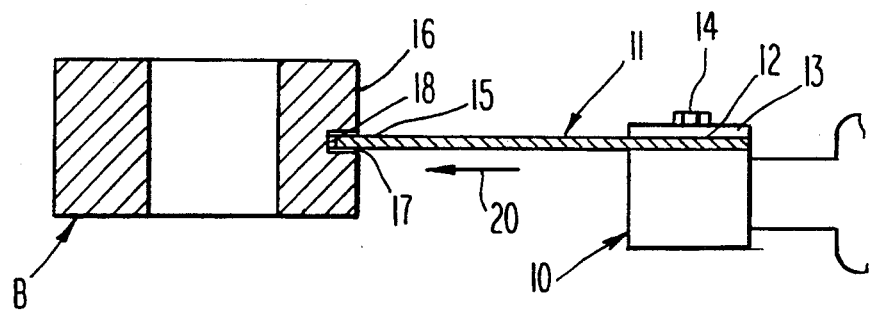
FIG. 1 is a schematic vertical sectional view, taken through a shaping apparatus of the bone saw type, showing a bone kerf being cut into a bone, with the tool being driven by a suitable oscillating driving apparatus, fragmentally illustrated, which tool is typical of prior art bone shaping apparatus.

Referring now to the drawings in detail, reference is made to FIG. 1, wherein a shaping apparatus is shown, of a type that is representative of the prior art, and in this instance, the same is shown as a bone saw apparatus. The saw apparatus will have a driving mechanism 10 which in the case of a bone saw, will preferably drive the saw member 11 in an oscillating motion, such as for example, similar to those disclosed in any of the above-mentioned patents, or for example, in U.S. Pat. No. 2,854,981, with the right-most end of the proximal or bone saw 11 being connected to the oscillating tool 10 at its end 12, by means of a suitable end plate 13 and fastener 14.

The bone B is shown to the left of FIG. 1, with the left end 15 of the saw penetrating the surface 16 of the distal or bone B to form a groove, indentation or the like, normally called a bone kerf 17, as the teeth 18 at the left end 15 of the saw 11 penetrate the bone B, moving leftward, or in the direction of the arrow 20 in FIG. 1.

Figure 2:
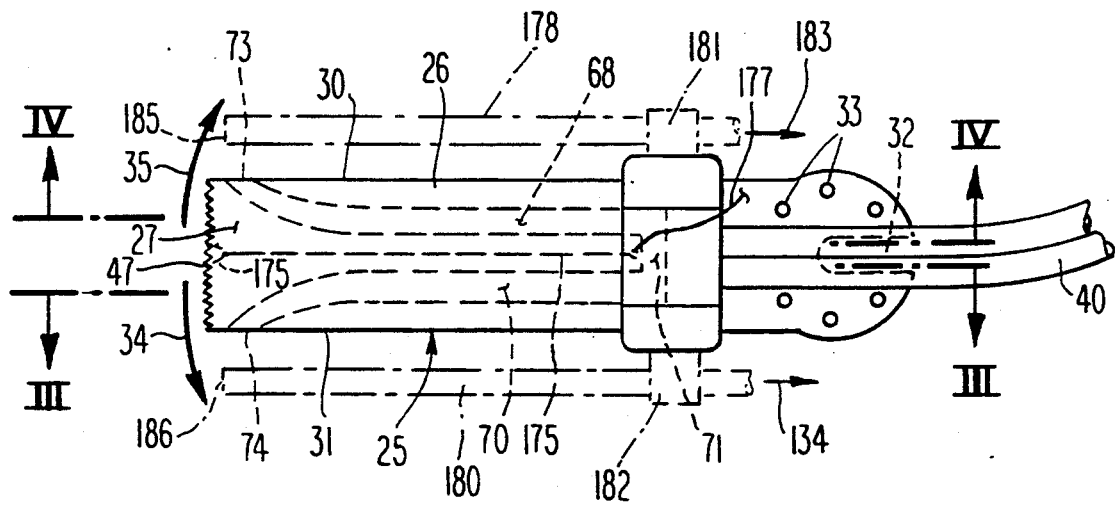
FIG. 2 is a top plan view of a bone shaping apparatus of the bone saw type, in accordance with this invention, wherein liquid cooling conduits within the bone saw are illustrated in phantom, and wherein scavaging conduits for scavaging away the results of bone shaping are likewise illustrated in phantom, on opposite sides of the full line illustration of FIG. 2.

Referring now to FIG. 2, a shaping apparatus in the form of a bone saw, in accordance with this invention, is provided, generally designated by the numeral 25. The shaping apparatus 25 includes a shaping member 26, which in this particular embodiment of the invention in which the shaping member is a bone saw, comprises a generally flat saw blade, having top and bottom wide side surfaces 27, 28 connected by narrow side surfaces 30 and 31.

The right or first end of the shaping member 26 is provided with a suitable slot 32 for attachment to the driving source or tool 10, and preferably with a plurality of bolt holes 33, for also assisting the securement of the same to a tool 10, whereby fasteners, bolts or the like may be received within the holes 33, and whereby after such attachment to a suitable driving source, the saw-type shaping apparatus 25 may be oscillated backwards and forward, in the directions of the arrows 34, 35 of FIG. 2. In the alternative to bolt holes 32, one or both major surfaces of the end 12 of the saw may be roughened, as by means of a frit-covering, or even a knurling for high frictional gripping or clamped engagement between the drive 10 and its end plate 13, with the end 12 of the saw therebetween.

Figure 3:
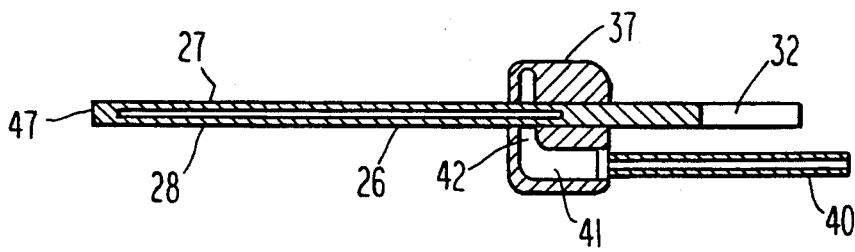
FIG. 3 is a vertical sectional view, taken through the apparatus of FIG. 2, generally along the line III—III of FIG. 2, and wherein gaseous fluid and liquid fluid delivery means is illustrated, via a manifold means.
Figure 4:
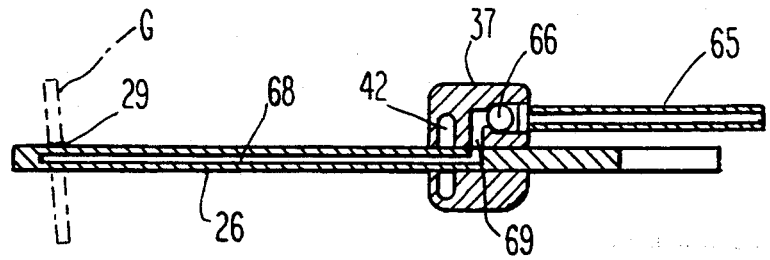
FIG. 4 is a view similar to that of FIG. 3, but taken along the line IV—IV of FIG. 3, and wherein the liquid delivery valve means is also illustrated.

The apparatus 25 includes a manifold member 37 extending above and below the surfaces 27, 26, respectively of the saw blade member 26, as shown in FIGS. 3 and 4, connected thereto by suitable means (not shown). The manifold 37 is a manifold for both gaseous fluid (preferably air) and liquid fluid (often water, with or without additives thereto, the most common of which is a saline solution).

Figure 6:
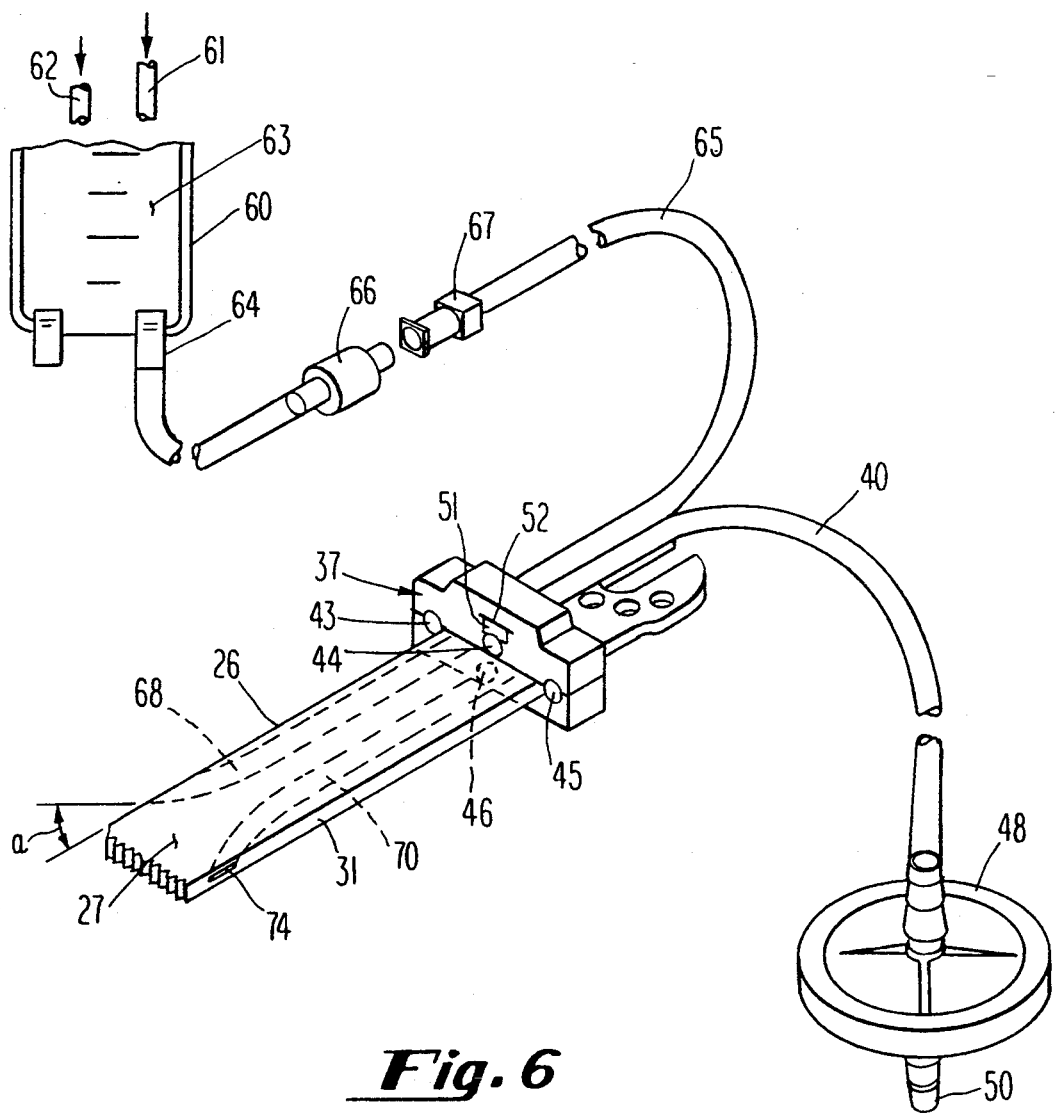
FIG. 6 is a top perspective view of a shaping apparatus in accordance with this invention, with gaseous fluid and liquid fluid delivery conduits thereto being illustrated.

With reference to FIG. 3, in particular, it will be seen that means are provided for supplying a source gaseous fluid, such as air, such means being in the form of a tube or like 40, which delivers the fluid to a zone 41 in manifold 37, which zone, in turn, is in communication for delivering the gaseous fluid into an upwardly extending zone 42 of the manifold, for discharge from the front (or left as viewed in FIGS. 3 and 4) of manifold 37 via upper and lower openings 44, 46, disposed, respectively, just above and below respective upper and lower saw blade surfaces 27, 28, as is more clearly shown in FIG. 6, in the direction of the second, or left-most end of the blade 26, at 47, where the saw teeth of the blade 26 are located.

Similarly, openings 43 and 45 are provided, as shown in FIG. 6, for discharge of gaseous fluid, preferably air, along respectively associated narrow side edges or walls 30, 31 of the shaping blade 25.

It is the discharge of gaseous fluid, preferably air, from tube 40 via zones 41, 42, and outwardly of the openings 43–46, that enables the formation of a moving air curtain, directing the air (or other gaseous fluid) away from the manifold 37, and along the outside perimeter surface of the blade 26, toward the teeth 47, which, in use, would be toward the bone kerf, such as that 17 in the bone B of FIG. 1, in operation. The curtain could be oxygen, if desired, to improve local oxygenation at the site of shaping. It is the curtain thus formed which enables the impingement of the same with aerosols (or sprays) emanating from a bone kerf as it is being abraded, to be continually urged back toward the bone kerf, and away from the surgeon or other medical professional generally handling the shaping apparatus 25, from the right end thereof, as viewed in any of FIGS. 2–6.

The air provided to the tube 40 will ordinarily have already passed through a bacteria filter, such as the 0.2 micron bacteria filter 48, shown in FIG. 6, which, in turn, is connected to a suitable air or other gaseous fluid supply, as at 50, to provide connection to a source of pressurized air.

It will be noted that the openings 43, 44, in particular, with an oscillating or pivotal movement of the blade 26 as shown in FIG. 2, serve to sweep the sides of the blade 26 throughout the arc provided by the oscillation, as the saw cuts bone.

It will also be noted that a baffle or deflector 51 is provided, pivotally mounted along one edge 52 thereof, as shown in FIG. 6, to partially overlie the opening 44, to provide adjustable positioning for the baffle 51 partially across the opening 44, so that some deflection of the stream of gaseous fluid, preferably air, from the opening 44, may be provided, to facilitate adjustment of the air curtain provided thereby. Similarly, the other openings 43, 45 and 46 may likewise be provided with a baffle or deflector 51, adjustably positionable partially thereover, if desired, although the same is not shown. In this manner, fine adjustment of the gaseous fluid curtain can be provided along all sides of the blade 26.

With reference now to FIGS. 2, 4, 4A and 6, it will be seen that liquid fluid, preferably an aqueous medium, a physiological balanced salt solution, or a saline solution or the like, if desired, generally containing some water is provided at 60, preferably from a delivery source, as at 61, for water or the like to moisten the bone, and a secondary source 62, for delivery of an additive to the solution 63 in the container 60, if desired, which additive may function as an antibiotic substance, or a solution to help promote bone growth, to help nourish and protect the fresh cut surface, the same being provided via line 62 into the container 60, as shown in FIG. 6 or the like. The discharge end 64 of the container 60 passes the liquid to line 65 via suitable connector fittings 66, 67, preferably of the quick-connect/disconnect type, whereby the liquid fluid, preferably water, is delivered to the manifold 37 via the line 65, which delivers the liquid to the manifold 37 through valve 66. After passing through valve 66, the liquid passes downwardly via vertical conduits 69, to enter horizontally conduits 68, 70 running substantially the length of the blade 26 from the manifold 37, to the left, or second, end of the blade 26 and terminating short of the left or distal end of the blade defined by the teeth or shaping means 47, as shown in FIG. 4, and as shown in phantom in FIG. 2, being fed via feeder conduit 71 as shown in FIG. 2. The discharge of the conduits 68 and 70 from the saw blade 26, is via openings 73, 74, respectively, shown in FIGS. 2 and 6, in the short or narrow sides 30, 31 of the blade that connect the wide sides 27, 28 thereof, in transverse cross-section to define an outside perimeter surface.

Figure 4A:
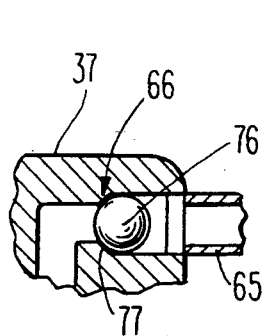
FIG. 4A is an enlarged fragmentary vertical sectional view of the valve illustrated in FIG. 4, shown enlarged for purposes of clarity.
Figure 5:
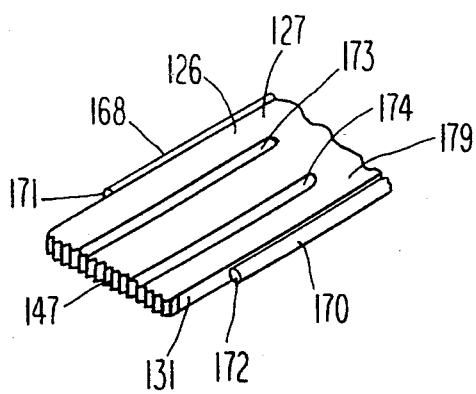
FIG. 5 is a fragmentary, top perspective view of an alternative liquid delivery system, along the sides of a saw blade, and with grooves being provided in the blade for discharge of products of the shaping operation, therealong and/or for heat dissipation.

With particular reference to FIG. 4A, it will be seen that the valve generally designated by the numeral 66, in the manifold 37, to which pressurized fluid, such as water or the like, is provided via line 65, comprises a ball 76, generally urged in seated engagement against a valve seat 75, by liquid pressure provided in line 65. The weight and size of the ball 76 may be selected, with due regard to such pressure, and with due regard for the amount of vibration that is set up upon oscillation of the blade when in use, such that such oscillation will normally cause the ball 76 to become unseated during operation of the tool due to such vibration, but that, when the tool is not operating and no oscillation occurring, the water pressure will again cause the ball 76 to seat against the valve seat 77.

with reference to FIG. 5, it will be seen that an alternative blade 126 is provided, with teeth 147, and wherein conduits 168,170 are provided on opposite narrow sides of the blade, rather than running down through the inside of the blade 126, as an alternative embodiment, with such external conduits 168, 170, terminating in liquid openings 171,172, otherwise functioning in the manner of the conduits 68, 70 of FIG. 6.

In the embodiment of FIG. 5, it will be noted that grooves 173,174 appear on the top surface 127 of the saw blade 126, and the same kind of grooves appear on the lower surface (now shown), in order to facilitate the passage of liquid and solid debris to or away from the bone kerf, or other shaped surface during cutting operations, with such particles of residue as a result of the bone shaping thereby being capable of being moved away from the kerf, or site of operation. It will also be noted that an air curtain similar to that provided via the gaseous fluid delivery system of FIGS. 2–4 is provided in the embodiment of FIG. 5, and that such curtain, particularly those portions thereof emanating from openings along the narrow sides 130, 131 of the blade 126, facilitate even further the guidance of liquid delivered via openings 171, 172, into the cut or kerf provided in the bone, just as air or other gaseous fluid delivered via openings 43, 45 in the embodiment of FIG. 6, facilitates the delivery of liquid discharged via openings 73, 74, in the embodiment of FIGS. 2 and 6.

With reference to FIG. 2, it will be seen that a sensor 175 is shown in phantom, embedded in the left-most end 47 of the blade, such sensor being adapted to record temperature, pressure, force, or sound, or any other desire parameter that corresponds to the shaping or cutting of the bone, during the bone shaping operation, and that the signal thus picked up by the sensor 175 is delivered via a signal delivery line 176, inside the saw blade 26, to a suitable exterior signal delivery line 177, to a suitable recordation device (not shown) for purposes of monitoring desired parameters during the shaping operation and adaptive control.

It will also be noted, with reference to FIG. 2 that scavenging conduits 178,180 may be provided, as shown in phantom in FIG. 2, carried by suitable respective mounting bosses 181, 182, that in turn are carried by the manifold 37, and that a suitable source of partial vacuum is provided to the conduits 178, 180, to create a suction or drawing effect in the direction of the arrows 183, 184, whereby liquids, with or without solid particles, such as bone debris and the like, may be withdrawn from the site of the operation, via scavenging inlet openings 185,186, to discharge, in order to clear the kerf or other area around the operation, for greater visibility of the operating personnel, for better treatment of the operating site, or both, as may be desired. It will be understood that the scavenging apparatus 178, 180, 181, 182, are optionally provided, and may be provided carried by the shaping apparatus 25 of this invention, or may be separate therefrom.

It will also be understood, while the means for generating the air curtain is preferably carried in the manifold 37 as described above, that such may, if desired, be provided in a separate fixture, rather than being specifically carried by the apparatus 25, as shown in FIGS. 2 and 6.

It will also be noted that the saw-tooth end of the blade 47 may be provided integral with the blade 26, or may be a separate member attached thereto. In the case where the same may be a separate member, such may be done in instances in which it is desired that the cutting teeth be constructed of a material different than that of the remainder of the blade such as diamond carbide or the like.

It will thus be seen that with the present invention, the part of the saw blade that is closest to the surgeon may be kept relatively dry and free of aerosols, in that the air openings blow water and small particles, such as aerosols, away from the user. It has been found that, with the device of the embodiment of FIGS. 2–6, for example, the side openings 43 and 45 are particularly effective to blow larger particles toward the bone and blow water away from the surgeon, and that upper and lower openings 44 and 45 produce a coanda effect to blow small particles and aerosols, as well as water, away from the surgeon or other user.

It will also be noted that, with particular reference to FIG. 6, the angle of discharge of liquid from the blade, along the narrow edges 30, 31 of the blade, will preferably be at an angle "a" of 30° or less to provide a forward component of motion for liquid being discharged from the blade, to facilitate driving the liquid toward the bone. As aforesaid, the air from openings, such as the opening 43, 45, likewise facilitates driving the liquid to the bone. It will further be noted that, if desired, the water or other liquid channels 68, 70 could be pressurized and/or pulsed (not shown), to have air behind them, to drive the water to the bone with greater force, or in a pulsing manner, and that such air being driven to the bone could be instead of, or in addition to air provided via the manifold 37 as shown in the illustrated embodiments. One way to provide air pressure behind the liquid would be to have the tubes 40, 65 interconnected, or to provide fluid communication between zones 42, 68.

It will further be noted that, while not shown in the embodiments illustrated, suitable shut-off controls may be provided for the air flow, either in the conduit 40, or within or on top of the manifold 37, to control the air flow in the blade, either by adjustment, by shut-off valve, or the like, as may be desired. In this regard, the control could occur in the form of a ball valve or the like, similar to that shown in FIG. 4A for liquid shut-off, at the inlet of the line 40 to the manifold 37 in FIG. 3, similar to that shown in FIG. 4, if desired.

In FIG. 4, there is also shown a saw guide "G", in phantom, having a slot 29 through which the blade 26 fits with minimal clearance, with the slot 29 having one side spring loaded (not shown) or otherwise constructed to maintain the clearance between the slot and saw to a minimum, to eliminate rocking of the saw in the guide, when the saw is in use and the guide is disposed against the bone B, clamped thereto or otherwise, as desired.

Similarly, adjustments for liquid and/or gaseous fluid supplied via the apparatus 25 may be controlled in a variable amount, or in an on/off manner, either manually, or by means of the sensing of any of a number of parameters via sensor 47, or in any other manner.

Furthermore, it will be noted that, particularly for, but not limited to, a shaping tool of the bone saw type, as illustrated herein, the larger surfaces 27, 28, but even, if desired, the narrower surfaces 30, 31, could be provided with a tetrafluoroethylene coating 179, to minimize friction as those surfaces interact with surfaces of bone, in cutting the bone kerf.

Generally, the surfaces of the saw blade are hardened, and most preferably are hardened steel. The hardening may be accomplished by any of various techniques, such as by nitriding, by neutron bombardment, or any other hardening, particularly surface hardening techniques known in the metalurgical arts.

Additionally, with particular reference to the embodiment of FIG. 5, it will be seen that the grooves 173, 174, whether or not used to partially carry away liquids and entrained solids from the site of operation, may also be effective as relieving grooves, to minimize heat that might otherwise be generated in the upper and lower (or larger) surfaces of the blade.

Additionally, while in the embodiments shown, the teeth 47 are illustrated as conventional saw-tooth cutting teeth, it will be understood that some tooth geometry provides better working conditions than others, particularly in an environment in which liquid is being provided for cooling purposes.

In practicing the present invention, it will be understood that, particularly where liquids are scavenged, as for example via lines 178, 180, such allows the option for collection of the liquid, its filtering and re-use, if desired.

It will also be noted that the liquid coolant provided to line 65, in addition to being water, or a water solution such as saline solution, may be provided with other treatments, such as antibiotics, anti-foam agents, agents that may produce foam, wetting agents to facilitate cooling provided by the liquid, thickeners and thinning agents for the liquid, or the like, all within the spirit and scope of the invention.

It will also be seen that the present invention provides a combination of fluid, as well as aerosol control, along with heat control for resulting in lower temperature shaping, insofar as the bone is concerned. Other details of the invention, its use and operation, selection of materials, and details of the delivery systems may all be provided in accordance with the present apparatus or modifications thereof, well within the spirit and scope of the invention as defined in the appended claims.

We claim:

1. A bone shaping apparatus for shaping bone during surgical operations, to create shaped bone, wherein the shaping produces undesirable heat generation in the vicinity of the shaped bone, the apparatus comprising:
    a) a bone shaping member;
    b) means on a proximal end of said shaping member for attachment of the member to a driving source for driving the member in oscillating shaping contact with bone;
    c) shaping means defining a distal end of said bone shaping member for shaping engagement with bone;
    d) said shaping member in transverse cross-section having two wide sides each connecting two narrow sides; and
    e) means cooperatively associated with said bone shaping member for supplying liquid fluid and delivering the liquid fluid toward the shaped bone along conduit means associated with said shaping member and opening through at least one opening located entirely on at least one of said two narrow sides and terminating short of said distal end.

2. The apparatus of claim 1, wherein the means for supplying liquid fluid is adapted for providing liquid comprised of at least some water.

3. The apparatus of claim 2, wherein the means for supplying and delivering liquid fluid comprises a liquid manifold means carried by said bone shaping member, with means connecting said liquid manifold means to a source of liquid, and wherein at least one liquid conduit means is provided from said liquid manifold means, passing at least partially through said shaping member to said at least one opening.

4. A bone shaping apparatus for shaping bone during surgical operations, to create a shaped bone, wherein the operations are carried out under conditions that aerosols are developed emanating from the shaped bone, and wherein the shaping produces undesirable heat generation in the vicinity of the shaped bone, the apparatus comprising:
   a) a bone shaping member;
   b) means on said shaping member for attachment of the member to a driving source for driving the member in shaping contact with bone
   c) shaping means on said bone shaping member for shaping engagement with bone;
   d) means cooperatively associated with said bone shaping member for supplying gaseous fluid along an external surface of said shaping member, and for delivering the gaseous fluid for impingement of the gaseous fluid with aerosols emanating from the shaped bone and driving the aerosols toward the bone;
   e) said shaping member in transverse cross-section having two wide sides each connecting two narrow sides; and
   f) means cooperatively associated with said bone shaping member for supplying liquid fluid and delivering the liquid fluid along conduit means associated with said shaping member and opening through at least one opening at at least one of said two narrow sides toward the shaped bone.

5. The apparatus of claim 4, wherein the means for supplying and delivering the gaseous fluid comprises means providing pressurized gas in the form of at least one gas curtain, and wherein the means for supplying liquid fluid is adapted for providing a liquid with at least some water.

6. The apparatus of claim 5, wherein the means for supplying and delivering the gaseous fluid comprises an air manifold carried by said bone shaping member; with means connecting said manifold to a source of pressurized air, and wherein at least one air opening is provided in said air manifold means, opening in a direction toward said bone shaping means, and wherein the means for supplying and delivering liquid fluid comprises a liquid manifold carried by said bone shaping member, with means connecting said liquid manifold means to a source of liquid, and wherein at least one liquid conduit means is provided from said liquid manifold means, passing at least partially through said shaping member to said at least one opening.

7. The apparatus of any one of claims 1 and 4, wherein the shaping apparatus comprises a saw apparatus, with said shaping member being a saw blade.

8. An apparatus according to any one of claims 1 and 4, including scavenging means disposed on the apparatus for scavenging substances resulting from the shaping operation.

9. An apparatus according to any one of claims 1 and 4, including valve means and seat means operatively associated with said means for delivering fluid, for opening and closing said means for delivering fluids therethrough, respectively.

10. An apparatus according to claim 9, with said valve means comprising means:
   a) responsive to fluid pressure force on said valve means to keep the valve means closed when the apparatus is not being driven by a said driving source, and
   b) responsive to motion set up in the shaping apparatus when the shaping apparatus is being driven by a said driving source to overcome the fluid pressure force and open the valve means.

11. An apparatus according to any one of claims 1 and 4, wherein at least one surface of said shaping member has a friction-reducing coating thereon, that comes into contact with bone during a shaping operation.

12. An apparatus according to any one of claims 1 and 4, wherein the means for supplying liquid fluid is adapted for providing a curative substance for enhancing a freshly shaped portion of bone.

13. An apparatus according to claim 4 including means carried by said apparatus for deflecting at least some gaseous fluid from the source thereof, sufficiently along said shaping member to facilitate increased cooling of said shaping member.

14. An apparatus according to any one of claims 1 and 4, including sensing means at said shaping member for sensing at least one parameter responsive to the shaping of bone, and means for delivering a signal from said sensing means to a measuring means.

15. An apparatus according to any one of claims 1 and 4, wherein at least one groove is provided in an exterior surface of said shaping member.

16. An apparatus according to claim 4, wherein said conduit means are disposed outside said bone shaping member.

17. A method of shaping living bone during surgical operations in which the shaping causes a shaped bone, wherein the operations are carried out under conditions in which aerosols can develop, emanating from the shaped bone, including the steps of:
   a) providing an apparatus including a bone shaping member having two wide sides connecting two narrow sides defining an outside perimeter surface;
   b) attaching the bone shaping member to a driving source for driving the member in shaping contact with bone;
   c) bringing the shaping member into contact with the bone and engaging the bone, to shape the same while the member is in contact with the bone; and
   d) supplying gaseous fluid along said outside perimeter surface of the shaping member and impinging the gaseous fluid with aerosols emanating from the shaped bone, to drive the aerosols back toward the bone.

18. The method of claim 17, wherein the step of supplying gaseous fluid comprises delivering the fluid from a manifold mounted to the bone shaping member.

19. The method of claim 17, wherein the step of supplying gaseous fluid comprises delivering the fluid from a source separate from the bone shaping member.

20. A method of shaping living bone during surgical operations in which the shaping causes a shaped bone, wherein the operations are carried out under conditions in which undesirable heat build-up can develop in the shaped bone, including the steps of:
a) providing an apparatus including a bone shaping member comprising shaping means defining a distal end of the bone shaping member;
b) attaching a proximal end of the bone shaping member to a driving source for driving the member in shaping contact with bone;
c) bringing the shaping member into contact with the bone and engaging the bone, to shape the same while the member is in contact with the bone:
d) providing the shaping member in transverse cross-section with the two wide sides each connecting two narrow sides; and
e) supplying a liquid fluid and delivering the liquid fluid toward the shaped bone along a conduit associated with the shaping member and opening through at least one opening at at least one of the two narrow sides, said opening terminating short of said distal end.

21. The method of claim 20, including the step of delivering a curative substance to the shaped bone, along with the liquid fluid, to enhance a freshly shaped bone.

22. The method of claim 20, including the step of providing a pulsing source of gas pressure to the liquid fluid for pulsing the liquid fluid delivery.

23. The method of claim 20, including the step of providing air to the liquid fluid.

* * * * *

UNITED STATES PATENT AND TRADEMARK OFFICE
CERTIFICATE OF CORRECTION

PATENT NO. : 5,409,491
DATED : April 25, 1995
INVENTOR(S) : John R. Boehringer, Wynnewood; John Karpowicz, Glenmoore:

It is certified that error appears in the above-indentified patent and that said Letters Patent is hereby corrected as shown below:

Column 3, line 60 after "end of the" --proximal or-- should be deleted;

Column 3, line 60 after "2,854,981," and before "with the" --proximal or-- should be inserted;

Column 3, line 65 at the beginning of the line before "left end" --distal or-- should be inserted;

Column 3, line 66 at the beginning of the line before "bone B" --distal or-- should be deleted.

Signed and Sealed this

Twenty-sixth Day of September, 1995

Attest:

BRUCE LEHMAN

*Attesting Officer*    *Commissioner of Patents and Trademarks*